US011388386B2

(12) United States Patent
Daniels

(10) Patent No.: US 11,388,386 B2
(45) Date of Patent: Jul. 12, 2022

(54) MOTION MONITORING SYSTEM

(71) Applicant: Equi+Poise Limited, Wiltshire (GB)

(72) Inventor: Toby Benjamin Daniels, Wiltshire (GB)

(73) Assignee: Equi+Poise Limited, Salisbury (GB)

(*) Notice: Subject to any disclaimer, the term of this patent is extended or adjusted under 35 U.S.C. 154(b) by 0 days.

(21) Appl. No.: 16/769,871

(22) PCT Filed: Dec. 4, 2018

(86) PCT No.: PCT/GB2018/053507
§ 371 (c)(1),
(2) Date: Jun. 4, 2020

(87) PCT Pub. No.: WO2019/110976
PCT Pub. Date: Jun. 13, 2019

(65) Prior Publication Data
US 2021/0185296 A1    Jun. 17, 2021

(30) Foreign Application Priority Data

Dec. 4, 2017  (GB) .................................... 1720165

(51) Int. Cl.
*H04N 13/243* (2018.01)
*A01K 29/00* (2006.01)
(Continued)

(52) U.S. Cl.
CPC ......... *H04N 13/243* (2018.05); *A01K 29/005* (2013.01); *G06V 20/52* (2022.01);
(Continued)

(58) Field of Classification Search
CPC ...... A61B 5/0077; A61B 5/11; H04N 13/243; H04N 13/275; A01K 29/00; A01K 29/005
See application file for complete search history.

(56) References Cited

U.S. PATENT DOCUMENTS

| 4,600,016 A | 7/1986 | Boyd et al. |
| 5,412,420 A * | 5/1995 | Ellis ..................... A01K 29/005 348/135 |

(Continued)

FOREIGN PATENT DOCUMENTS

| AU | 2017200769 A1 | 3/2017 |
| DE | 4418475 A1 | 11/1995 |

(Continued)

OTHER PUBLICATIONS

International Search Report dated Feb. 21, 2019 in PCT Application No. PCT/GB2018/053507.

(Continued)

*Primary Examiner* — Rowina J Cattungal
(74) *Attorney, Agent, or Firm* — Occhiuti & Rohlicek LLP

(57) ABSTRACT

An imaging system is provided, the imaging system is configured to generate video streams of a moving target in a predefined area, the imaging system comprising: first and second image capture devices configured to be movable and to capture first and second video streams of the moving target from a first direction; third and fourth image capture devices configured to be movable and to capture third and fourth video streams of the moving target from a second and third directions, the second and third directions being substantially opposite to one another and substantially perpendicular to the first direction; a fifth image capture device configured to be stationary and to capture a fifth video stream of the moving target from a fourth direction, the fourth direction being substantially perpendicular to the first to third directions; and a controller configured to move the first to fourth image capture devices along with the moving target in the predefined area.

32 Claims, 4 Drawing Sheets

(51) Int. Cl.
*H04N 13/275* (2018.01)
*H04N 5/247* (2006.01)
*G06V 20/52* (2022.01)
*G06V 40/10* (2022.01)

(52) U.S. Cl.
CPC ............ *G06V 40/10* (2022.01); *H04N 5/247* (2013.01); *H04N 13/275* (2018.05)

(56) References Cited

U.S. PATENT DOCUMENTS

| | | | |
|---|---|---|---|
| 6,231,527 B1 | 5/2001 | Sol | |
| 7,601,126 B2* | 10/2009 | Keegan | A61B 5/0002 |
| | | | 600/595 |
| 2005/0015002 A1 | 1/2005 | Dixon et al. | |
| 2005/0257748 A1* | 11/2005 | Kriesel | A22B 5/007 |
| | | | 119/51.02 |
| 2009/0080598 A1 | 3/2009 | Tashman et al. | |
| 2012/0253201 A1* | 10/2012 | Reinhold | H04N 13/254 |
| | | | 345/419 |
| 2012/0274442 A1* | 11/2012 | Mottram | A01K 29/005 |
| | | | 340/5.8 |
| 2014/0350410 A1* | 11/2014 | Axelsson | A61B 5/0077 |
| | | | 600/476 |
| 2015/0085131 A1 | 3/2015 | Anderson | |
| 2016/0029648 A1* | 2/2016 | Schmitzek | G06V 10/42 |
| | | | 348/135 |
| 2016/0066820 A1 | 3/2016 | Sales et al. | |
| 2016/0073614 A1 | 3/2016 | Lampe et al. | |
| 2020/0077667 A1* | 3/2020 | Lauridsen | A22B 5/0064 |

FOREIGN PATENT DOCUMENTS

| | | |
|---|---|---|
| JP | H07135586 A | 5/1995 |
| JP | H90284613 A | 10/1997 |
| JP | 2004336186 A | 11/2004 |
| KR | 1020100124640 A | 11/2010 |
| KR | 20130120663 A | 11/2013 |
| WO | 2012/107620 A1 | 8/2012 |
| WO | 2012/109244 A1 | 8/2012 |

OTHER PUBLICATIONS

British Search Report dated Feb. 27, 2017 in GB Application No. 1620638.5.

British Search Report dated May 31, 2018 in GB Application No. 1720165.8.

* cited by examiner

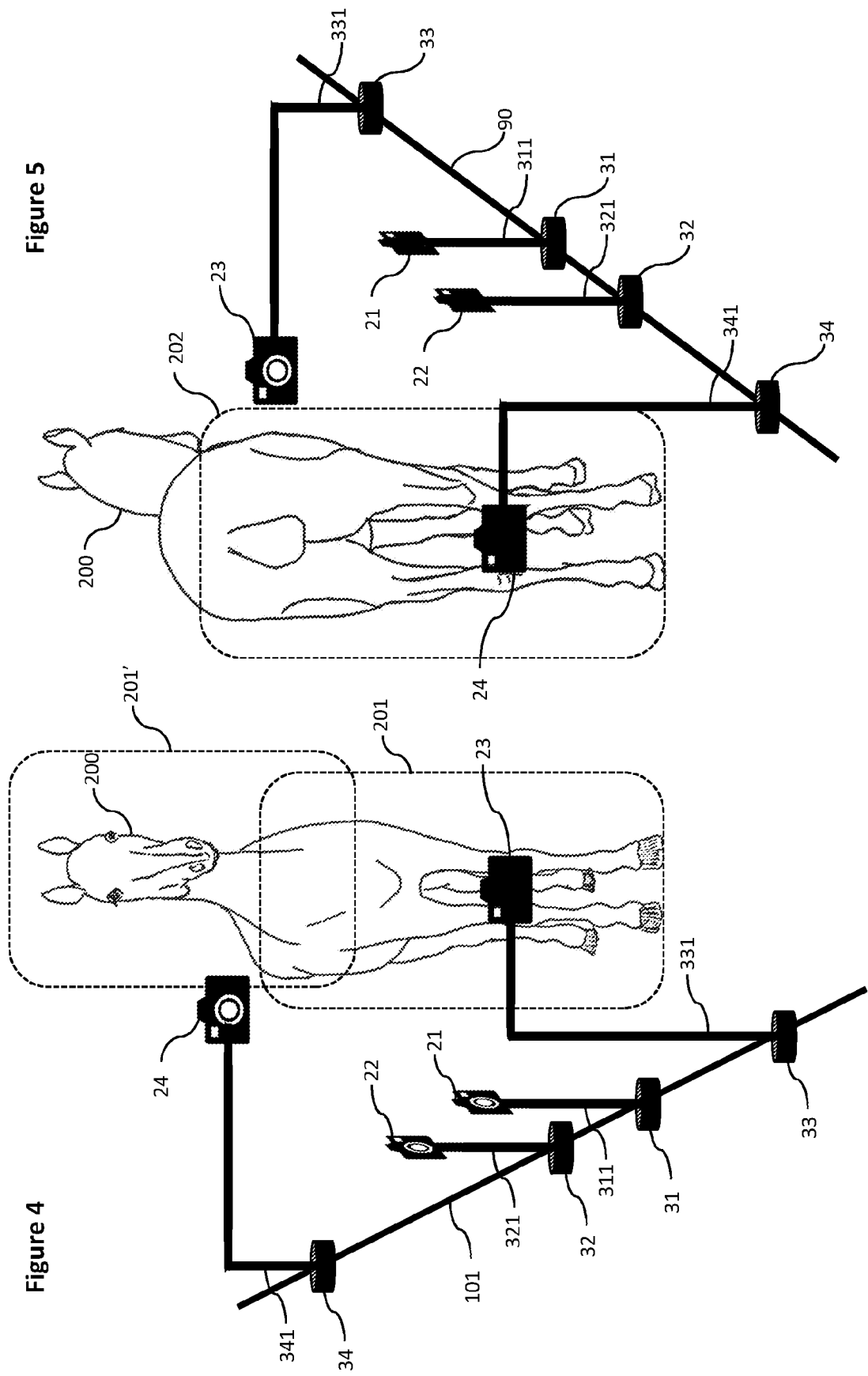

MOTION MONITORING SYSTEM

CROSS-REFERENCE TO RELATED APPLICATIONS

This application is a national phase under 35 U.S.C. 371 of International Application No. PCT/GB2018/053507 filed on Dec. 4, 2018, which claims priority to British Application No. 1720165.8 filed on Dec. 4, 2017, the contents of all of which are hereby incorporated by reference in their entireties.

The present invention relates to a motion monitoring system comprising an imaging system for generating video streams of a moving target in a viewing zone of a predefined area, and in particular to a motion monitoring system for a moving quadruped such as an equine.

BACKGROUND

Within the animal husbandry and training world, the study of the physiology of an animal is of great importance. In the training world, for example, the potential of young animals, such as horses, as good racing animals may be determined based on their physiological capabilities. In equestrian sports, for instance, this information can be used in a horse's physical development and training. For example, equine conformation evaluates the degree of correctness of a horse's bone structure, musculature, and its body proportions in relation to each other. Undesirable conformation can limit the horse's ability to perform a specific task. Although there are several universal faults, a horse's conformation is usually judged by what its intended use may be. A horse with poor form for a Grand Prix show jumper could have excellent conformation for a World Champion cutting horse, or to be a champion draft horse.

Alternatively, when it comes to maintaining the general health and wellbeing of an animal the monitoring of the animal's physiology allows for the detection and subsequent treating of any abnormalities or irregularities. For example, lameness is an abnormal gait or stance of an animal that is the result of dysfunction of the locomotor system and is a common veterinary problem in racehorses, sport horses and pleasure horses. It is one of the costliest health problems for the equine industry, both monetarily for the cost of diagnosis and treatment and for the cost of time off resulting in loss of use. Gait is evaluated for symmetry. This includes the overall fluidity of the horse's motion, length of stride, loading of a leg, how the hoof lands on the ground (flat, toe, or heel-first), range of motion of the joints, deviations in body position, and position of the head and neck.

One way of detecting lameness is by evaluating the animal in motion, usually during a walk and trot, but also during a canter. Assessment of the trot is a good way of localizing the lameness to a particular leg, because it is a symmetrical gait where the front half of the horse and the back half move in unison. Assessment of the canter is also useful as it highlights any resistance to picking up the canter or to engage the hind end—suggesting pain in the sacro-iliac joint, pelvis or hind leg.

Lameness may be accentuated under certain conditions. Therefore, the moving examination is often performed both in a straight line and on a circle, and may be repeated on different footings. Hard footing tends to make joint and bone injury more apparent, while soft, deep footings tend to accentuate soft tissue injury. Circles may accentuate a lameness when the lame leg is on the inside or outside of the circle. At times, it may be helpful to evaluate the horse under saddle, since the weight of the rider can accentuate lameness. In cases of decreased performance, it can be useful to watch a horse performing certain discipline-specific movements, which may be the only time the rider notices a change in the horse's abilities.

Repeated visual observations of the animal in motion are, therefore, necessary to observe all the various elements of motion so as to make an assessment. Video recordings of the animal in motion are thus an effective way of carrying out these evaluations and such recordings advantageously reduce the number of repetitions that may be needed on the part of the animal for any given movement. One way of obtaining such video recordings is with the use of a video camera operated by a camera operator while the rider or trainer rides or interacts with the animal. Alternatively, the camera may simply be mounted on a support and set to record. The support may be stationary, or it could be a motorized panning stand that tracks the animal as the animal moves around a predefined area such as a racing track, a riding arena or an arena for schooling. In some systems, to provide multiple views, several cameras are mounted onto the same motorized support to move the cameras collectively.

Using camera operators, however, can be costly or impractical for long sessions. Additionally, the quality of the video will be dependent on the skill of the operator thus the quality of the video can be inconsistent.

The problem with using a single camera mounted to a support is that to ensure the subject (e.g. a horse with or without its trainer or rider) stays within the camera's field of view while moving around in the predefined area, the camera lens must be set to a fixed wide zoom. Consequently, the subject will appear too small on the viewing screen to allow close examination of the subject's anatomy. Alternatively, for a detailed view, the lens must be fixed at a longer focal length. But this will have the problem of the subject coming in and out of the field of view of the camera lens and it will not be possible to produce a continuous recording of the desired aspect of the subject's anatomy (e.g. the shoulder muscles) for examination.

To obtain the most accurate assessment of the animal's physical attributes, there is a need for a monitoring system with an imaging system that can produce clear and continuous recordings of the animal's physical attributes from a variety of viewing points while the animal is moving around.

SUMMARY OF INVENTION

In a first aspect, an imaging system is provided, the imaging system is configured to generate video streams of a moving target in a predefined area, the imaging system comprising: first and second image capture devices configured to be movable and to capture first and second video streams of the moving target from a first direction; third and fourth image capture devices configured to be movable and to capture third and fourth video streams of the moving target from a second and third directions, the second and third directions being substantially opposite to one another and substantially perpendicular to the first direction; a fifth image capture device configured to be stationary and to capture a fifth video stream of the moving target from a fourth direction, the fourth direction being substantially perpendicular to the first to third directions; and a controller configured to move the first to fourth image capture devices along with the moving target in the predefined area.

Each image capture device may be configured to be movable independently of the other image capture devices.

Each image capture device may have a degree of freedom and the controller is configured to articulate each image capture device using that degree of freedom to track the motion of the moving target. Each image capture device may be configured to be articulated independently of the other image capture devices.

The imaging system may comprise a sixth image capture device configured to capture a video stream of the moving target from a fifth direction, the fifth direction being substantially opposite to the first direction. The sixth image capture device may be stationary.

The imaging system may further comprise a seventh image capture device spaced apart from the fifth image capture device and configured to capture a video stream of the moving target from the fourth direction.

The first and second image capture devices may be positioned alongside each other. The image capture devices may be configured to be spaced apart from one another in dependence on the size of the moving target. The controller may be configured to maintain a relative distance between the image capture devices in dependence on the size of the moving target.

The first to fourth image capture devices may be configured to be aligned horizontally. Each of the image capture devices may be mountable onto a respective driving element. Each of the image capture devices may be mountable onto their respective driving elements using a respective support mechanism.

Each image capture device may comprise a sensor, the sensor being configured to sense a distance between its image capture device and another object. The controller may be configured to determine a predefined distance between each image capture device and the other object in dependence on the sensed distance between each image capture device and the other object. The controller may be further configured to maintain a relative distance between each of the image capture devices and the other object in dependence on the determined predefined distance when the image capture devices are being moved.

The other object may be another image capture device. The other object may be the moving target.

The controller may further be configured to produce a three-dimensional (3D) video stream of the moving target using the video streams from the first, the second and the sixth image capture devices.

The imaging system may further comprise a track covering the predefined area's perimeter along which the image capture devices are moved. The first to fourth image capture devices may be slidably mounted onto the track. The controller may further be configured to move the first to fourth image capture devices at a speed corresponding to the moving target's speed.

In a second aspect, a motion monitoring system is provided, the motion monitoring system is configured to assess the motion of an equine in motion, the motion monitoring system comprising the imaging system described above, with the equine being the said moving target.

The first to fourth image capture devices may be configured to be aligned with the equine's limbs. The first image capture device may be configured to provide a field of view of a lower aspect of a shoulder to a hoof surface of a foreleg of the equine. The first image capture device may be configured to provide a field of view of an upper aspect of the ears to the shoulders of the equine. The second image capture device may be configured to provide a field of view of a stifle to a hoof surface of a hindleg of the equine. The third image capture device may be configured to provide a field of view of a lower aspect of the shoulders to the hooves of the forelegs and the chest of the equine. The fourth image capture device may be configured to provide a field of view of the rump to the hooves of the hindlegs of the equine. The fifth and seventh image capture devices may be configured to provide a field of view of the head to the rump of the equine. The sixth image capture device may be configured to provide a field of view of one side of the equine opposite to that provided by the first and the second image capture devices.

In a third aspect, a method of generating video streams of an equine in motion in a viewing zone of a predefined area is provided, the method comprising: capturing first and second video streams of the equine in motion from a first direction with a first and second image capture devices; capturing third and fourth video stream of the equine in motion from a second and third directions with a third and fourth image capture devices, the second and third directions being substantially opposite to one another and substantially perpendicular to the first direction; capturing a fifth video stream of the equine in motion from a fourth direction with a fifth image capture device, the fourth direction being substantially perpendicular to the first to third directions; and moving the first to fourth image capture devices along with the equine in motion in the predefined area.

The present invention will now be described by way of example with reference to the accompanying drawings in which:

FIG. 4 shows a schematic illustration of the imaging system of FIG. 2 from a front view of the animal being assessed.

FIG. 5 shows a schematic illustration of the imaging system of FIG. 2 from a rear view of the animal being assessed.

DESCRIPTION

In the motion monitoring system to be described below, the physical attributes of a moving target such as an equine can be assessed by utilizing recorded video images of the animal while it is being moved around or exercised in a predefined area such as an arena for schooling, a hall, a race track, etc. FIGS. 1 to 4 show an example of the imaging system implemented in a horse riding school.

Figure 1:
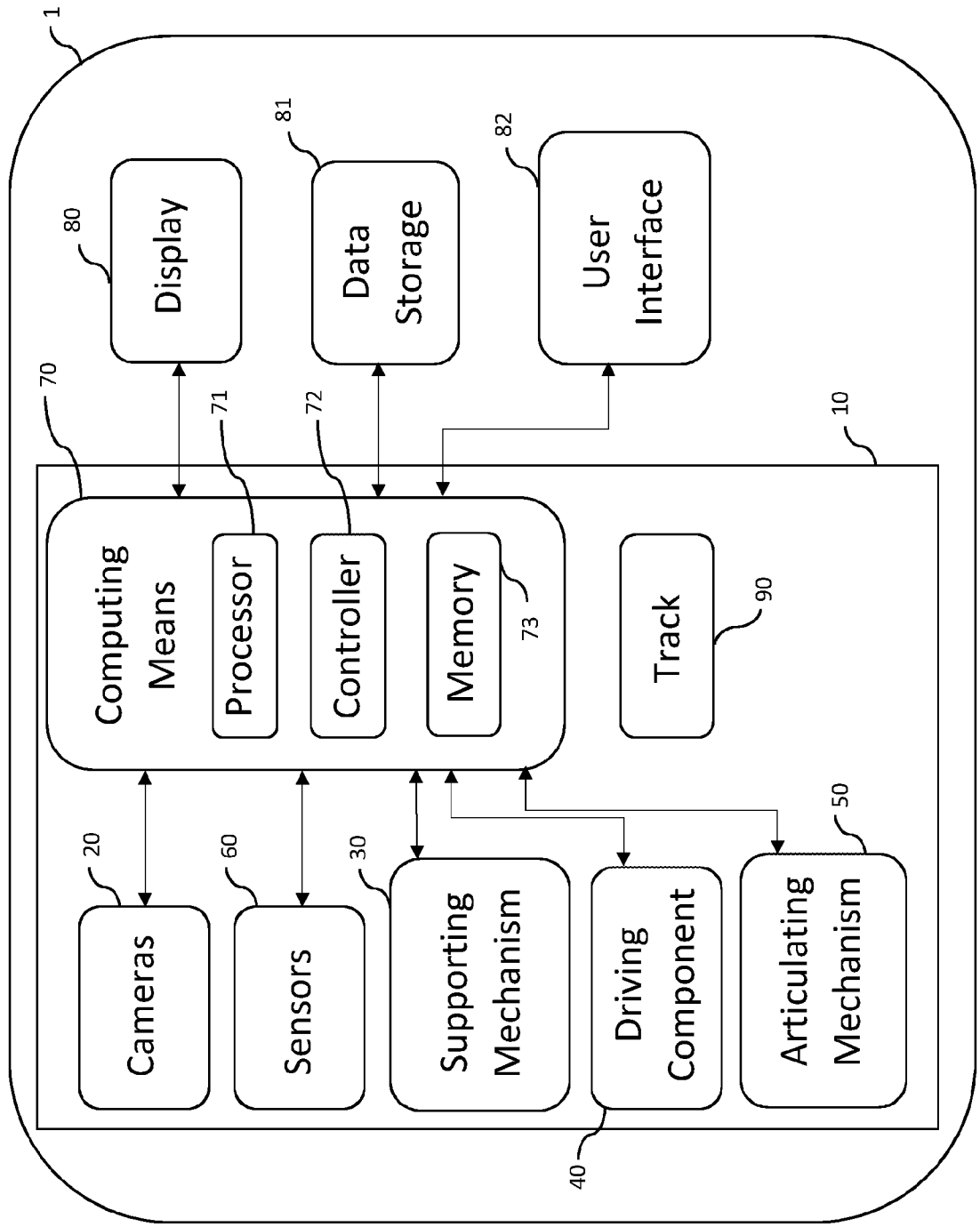
FIG. 1 shows a schematic illustration of an example of the motion monitoring system.

Turning to FIG. 1, an example of a motion monitoring system 1 for assessing an equine such as a horse is shown. The motion monitoring system 1 includes a portable imaging system 10 for generating multiple video streams of a target, in this case a horse 200, from various fields of view to produce continuous, clear, and in focus recordings of the horse throughout its session in a predefined area 100 for later assessment. The imaging system 10 comprises a plurality of image capture devices such as video cameras 20 for capturing video streams of the horse 200 as it moves around the predefined area 100. The video cameras 20 are mountable onto respective supporting mechanisms 30 that may include a driving component 40 for following the horse 200 as it moves around in the predefined area 100. The supporting mechanisms 30 are driven on a track 90 placed in the predefined arena 100. The video cameras 20 may be a fixed type where their viewing angle is fixed. The video cameras 20 may have one or more degrees of freedom by being equipped with an articulating mechanism 50 that allows the cameras 20 to be articulated to aim at the moving target. The articulating mechanism 50 may be a pan-tilt-zoom mechanism that gives each video camera 20 the maximum degrees of freedom of motion for controlling their viewing angles and the ability to zoom in and out for proper framing of the moving target. The pan and tilt feature also allow the video cameras 20 the ability to track and follow the target as it moves around the predefined area 100. The imaging system 10 further includes sensors 60 for target and/or motion detection or for detecting the relative distance between the cameras 20 or between the cameras 20 and other objects such as the moving target.

All data generated from the cameras 20, sensors 60, supporting mechanisms 30, driving components 40, and articulating mechanisms 50, etc. of the imaging system 10 is provided to a suitable computing means 70 which may be a microprocessor or a microcomputer. The computing means 70 processes this data with the aid of one or more processors 71. The processed data is used by a controller 72 to generate outputs such as a stream of distance estimates, a plurality of video streams or movement instructions for the articulating mechanisms 50 to track and for the driving components 40 to drive the supporting mechanisms 30 to follow the horse 200. The computing means 70 includes a memory 73 for saving the incoming and outgoing data.

The motion monitoring system 1 further includes a display 80 such as a TV or computer monitor for visually displaying the generated video streams. A user interface 82 such as a graphical user interface may be provided so that a user may input such information as the type and size of the target to be tracked or the required relative distances that are to be maintained between the video cameras 20 and the target as it moves in the predefined area 100. A data storage medium 81 may be provided for recording the generated video streams.

Equestrian sporting manoeuvres require a fairly sizable area in which to execute the athletic manoeuvres. This can be directly attributed to the size of the animal and the precision with which such manoeuvres must be carried out, often requiring several strides for set-up before execution of a manoeuvre. For this reason, simply setting a camera on a tripod, or installing one or more cameras, in the arena, and recording the session too often yields a video sequence that is out of focus, out of view, or obstructed for large parts of the session.

When assessing the correctness of an exercise being performed under saddle, viewing the horse and its rider from the above, the front and the side will provide the instructor or the trainer with important information.

When assessing lameness, a classic sign of lameness in a front leg is a prominent "head bob". Viewed from the side, the horse raises its head and neck when the lame leg hits the ground, which helps to unload the lame leg. A head bob is usually easy to see when one leg is lame, but can be subtle in very mild unilateral lameness, or in the case of bilateral front limb lameness. A horse may also try to reduce impact on a lame front leg by tensing of the muscles of the shoulder. In this case, it will stiffen the limb just before it hits the ground, a sign that may be noticed by an astute observer.

Evaluation of hind limb lameness can also be difficult. The viewer needs to watch the hip, sacrum, gluteal muscles, or hemi-pelvis (pelvis of one side of the body) when examining lameness in the hind end. Examination should be performed both watching the horse from behind while trotting away from the examiner, and from the side as the horse passes.

When watching from behind, the viewer often looks for a "hip hike" or "pelvic hike". This occurs when the horse raises the pelvis on the lame side as it is bearing weight, trying to shift weight from the painful leg in a manner similar to raising of the head in front limb lameness. This is a sudden, short upward motion of the hemi-pelvis or gluteal muscles. The hip of the lame leg does not always rise above the level of the hip of the sound leg, which can be confusing to those looking for a "hip hike". Instead, it is an exaggerated upward movement that is watched for during weight bearing. Additionally, horses with a hind limb lameness will tend to reduce the degree of leg use. To do so, some horses will reduce the contraction time of the gluteals on the side of the lame leg, leading to a "hip roll" or "hip dip" and appearance that the hip drops a greater degree on the side of the lame leg.

Sometimes, musculoskeletal pain which can be difficult to detect can be the cause of lameness and poor performance. Owners, riders, trainers and some vets are known to struggle with recognising when a horse is lame from looking at a horse's gait alone, and some lameness is so subtle that only an expert eye can see it. Owners, riders and trainers can also have a poor ability to recognise signs of pain seen when horses are ridden. As a result, problems are often labelled as training-related or behavioural, or deemed 'normal' for that horse because 'that's how he's always gone'. That means pain-related problems are often disregarded, the horse continues in work, and the problem gets progressively worse. If pain goes unrecognised and is not referred to a lameness specialist early enough, problems become too advanced to be resolved, or managed as well as they might have been if spotted sooner.

Recent studies suggest that it is possible to identify signs of pain from a horse's facial expressions when being ridden. Facial expressions include the ears, eyes, nose, muzzle, mouth and head position. Each body part can display an expression which may be normal, or reflect pain, conflict behaviour or distress. Recognition of changes in facial expression could, therefore, potentially save horses from needless suffering and chronic injuries, by enabling owners and trainers to recognise pain sooner, and getting these horses the veterinary care that they need.

As well as assessing the correctness of an exercise and detecting problems such as lameness, assessing the movements of the animals can also help our understanding of the muscle groups involved when the animal transitions from one type of movement to another. For example, it is still not understood how horses transition from a trot to a canter. When using static cameras as well as focusing issues not enough information can be obtained to allow for a proper analysis of the movements involved. For example, using a static camera a recording could be made of around 4 trot strides and 1 canter stride which does not provide an examiner with enough information. Additionally, it is not always possible for a trainer or rider to get the horse to transition at the moment they wish it.

Thus, to obtain the most accurate assessment of a horse's capabilities, it is desirable that the horse be filmed from a variety of angles and at a variety of gaits. Accordingly, it is desirable to film the horse from the front, the sides, the rear and from above at a walk, trot, canter and a gallop with the cameras 20 filming all its movements. The inventors have found that a minimum of 5 video cameras (arranged as described below) are required to obtain the required information.

The motion monitoring system 1 can use the data obtained from the video cameras 20 to generate conformation information and to identify any asymmetries in conformation that may have a factor with regards to gait, range of movement and ability to remain sound for certain activities. The video cameras 20 may be capable of capturing three-dimensional footage which could be achieved by using stereoscopic imaging devices.

Figure 2:
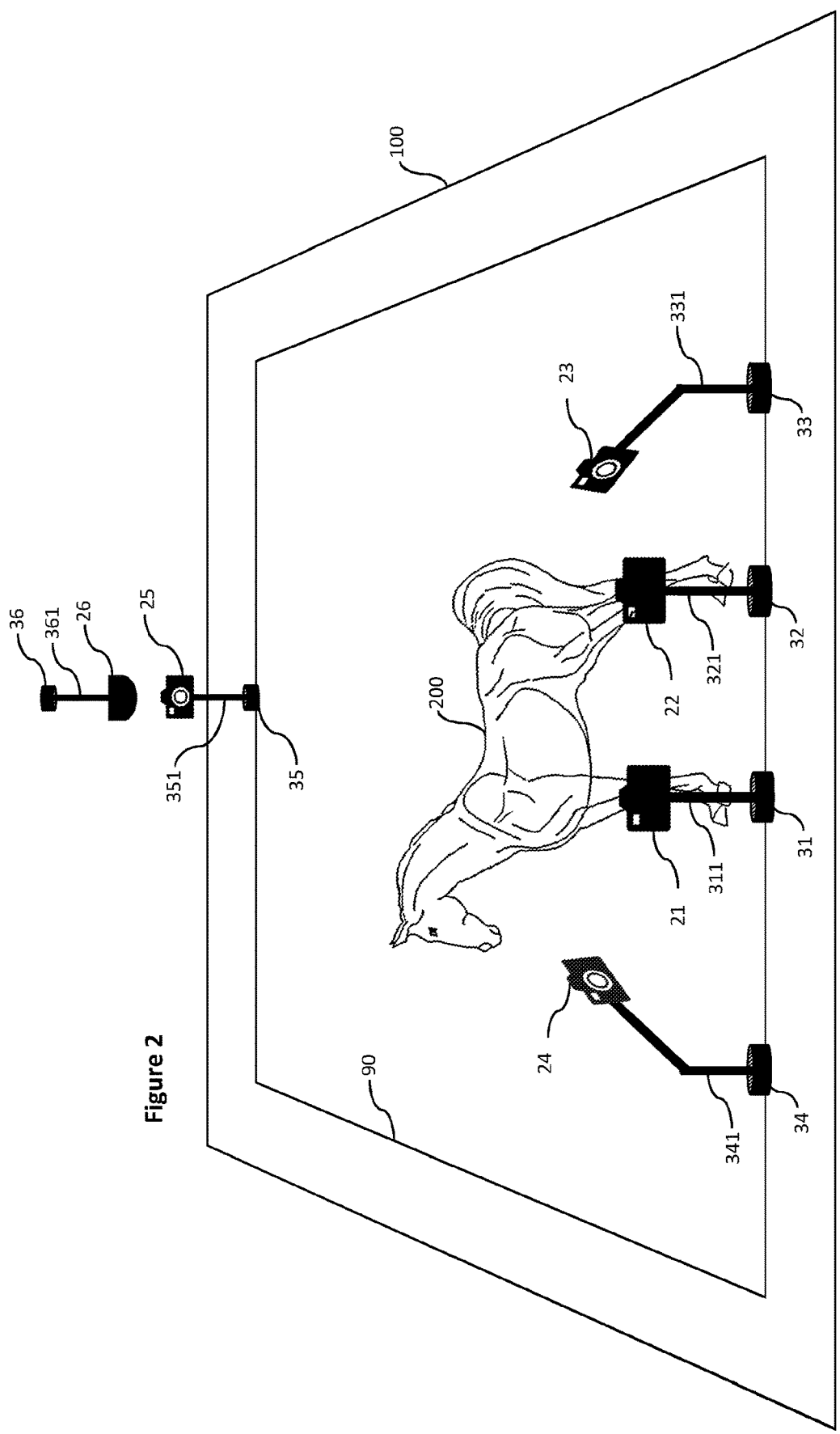
FIG. 2 shows a schematic illustration of various aspects of an example of the imaging system including an animal being assessed in an example of a predefined area with a plurality of cameras on a track.

FIG. 2 shows an exemplary predefined area 100. A track 90 is setup to cover the perimeter of the predefined area 100 in which the horse 200 will be assessed. The predefined area 100 and the track 90 can be of any shape. In FIG. 2 the track 90 is shown as substantially rectangular. The track 90 may have curved corners to provide a smooth transition for the video cameras 20 going around its corners. The track 90 may be shaped so as to follow the perimeter of the predefined area 100 in which it is installed.

The track 90 may be a rail such as a monorail. In this way fewer equipment is required to setup the imaging system 10 with the system typically being smaller, therefore, being less likely to startle an animal that may not be used to moving equipment. The track 90 may be covered with resilient rubber material so as to protect the animal from serious injury should the animal collide with it. The track 90 may be installed on a vertical surface such as the walls of a schooling arena. Preferably, the track 90 is installed on the ground of the predefined area 100 to avoid any problems associated with providing a continuous track around the whole of the arena as a result of features such as entrance and exit openings or wall mounted equipment or furniture.

In substantially the centre of the top of the predefined area 100 is positioned a video camera 26 to capture a top view video footage of the moving target. Video camera 26 provides a field of view of the entire horse 200 as it moves around the predefined area 100 from above. Video camera 26 provides such information as how the head is held, any movement of the head to the left or the right of its body, swaying of the back (usually causing high head carriage and stiffness through the back and often associated with weakness of ligaments of the back—it can also position a rider behind the centre of gravity, interfering with balance), spinal issues, back muscles, as well as rider position (whether a rider is slumped to the side thus putting sideways pressure on the back of the horse) and saddle fit. Video camera 26 may be mounted to a rotatable supporting mechanism 36. Alternatively, the supporting mechanism 36 may be stationary.

Video cameras 21 and 22 are positioned on one side of the predefined area 100 to capture video streams of the same side of the horse 200. Video camera 21 is positioned so as to be substantially aligned (in a horizontal direction) with the forelimbs of the horse 200. Camera 21 is positioned so as to be immediately laterally of the forelimbs of the horse with respect to the horse's intended direction of motion. Video camera 21 provides a field of view from around the lower aspect of the horse's shoulder (the scapula and the associated muscles) to around the hoof surface which is typically a span of about a meter in height, but which can vary from animal to animal. Different fields of view allow for the assessment of different aspects of motion. Video camera 21 provides information on the movement of the knee including any excessive or lack of rotation in the knee in both the forwards and backwards directions (often indicative of arthritis), the rotation of the shoulder, the fetlock joint, the pasterns (help disperse the concussive forces of the horse's step and vital in shock absorption), the hoof and cap shoe. This allows an examiner to examine the landing and falling of the lateral aspect of the forelimbs, the angle of the shoulder which has a great effect on the horse's movement and jumping ability and which is an important aspect of equine conformation, as well as issues such as a flared hoof wall or seeing shock waves going up the limb as the animal is put through its paces.

Video camera 22 is positioned so as to be substantially aligned (in a horizontal direction) with the hind legs of horse 200. Camera 22 is positioned so as to be immediately laterally of the hindlimbs of the horse with respect to the horse's intended direction of motion. Video camera 22 provides a field of view from around the stifle to around the surface of the hoof of the hindlegs which is typically a span of about a meter in height, but which can vary from animal to animal. Video camera 22 provides such information as allows an examiner to examine the landing, falling and movement of the hindlegs. A horse's "action" (most often used to describe the motion at the trot but also sometimes applied to the canter or gallop) is determined by the way the horse elevates its legs, knees, hock and feet and how it uses its shoulder, humerus, elbow and stifle. Video camera 22 provides similar information on the lower limbs as video camera 21 as well as information on the pelvic movements in both the forwards and backwards directions during canter, any stifle injuries, the hock and fetlock movement.

An examiner may assess the information provided from the various cameras either in isolation or in combination. As an example, by looking at any differences of movement between the information obtained from video camera 21 as compared to the information obtained from video camera 22 an assessment can be carried out as to whether the horse is over or under tracking or whether its motion is well regulated.

Video cameras 23 and 24 are positioned so as to capture images from behind and front of the horse 200 respectively. Video camera 23 is positioned so as to be substantially aligned with the centre of the back of the animal such that all four limbs are visible during filming. Video camera 23 provides a field of view 202 (see FIG. 5) from around the rump to around the hoof and allows an examiner to see video footage of how the legs work from behind to detect any issues such as dishing, lameness and incorrect footfall.

Video camera 24 is positioned so as to be substantially aligned with the centre of the front of the animal such that all four limbs are visible during filming. In this configuration, video camera 24 provides a field of view 201 (see FIG. 4) from around the shoulder to around the hoof of the animal and allows an examiner to see video footage of how the shoulders move and how the legs land (in particular the medial-lateral landing which can indicate any side-to-side imbalances leading to uneven forces across the hoof and uneven loading of the lower limb joints). Information about the way the legs land and its implications on the hoof structure is very important when it comes to shoeing horses. Additionally, issues such as any dishing from the shoulders, knees or fetlocks can be detected and the way in which the muscles in the upper part of the body affect the lower limbs that don't have much of a muscle mass can be studied. For example, the overall shape of a horse's chest plays a key role in the front leg movements. Also, the chest width allows for lung expansion and determines agility. Optionally, video cameras 21 to 24 are positioned so as to be horizontally aligned with one another.

Alternatively, video camera 24 may be positioned so as to be substantially aligned with the centre of the shoulders of the animal such that the head, the neck and the shoulders of the animal are visible during filming. In this configuration, video camera 24 provides a field of view 201' (see FIG. 4) from around the top of the ears to around the chest of the animal and allows an examiner to see video footage of the animal's facial expressions. This helps identify different expressions in a horse, such as the positions of the ears (e.g. ears being put back), changes in the eyes (e.g. partially or fully shut, showing the whites of the eyes or an intense stare), flaring of the nostrils, tightness in the muzzle, tipping of the head, tension around the eyes, an open mouth with exposed teeth, and/or being extremely above the bit. These expressions can be indicative of the animal being in pain and could thus potentially save horses from needless suffering and chronic injuries, by enabling owners and trainers to recognise pain sooner, and get these horses the veterinary care that they need.

Figure 3:
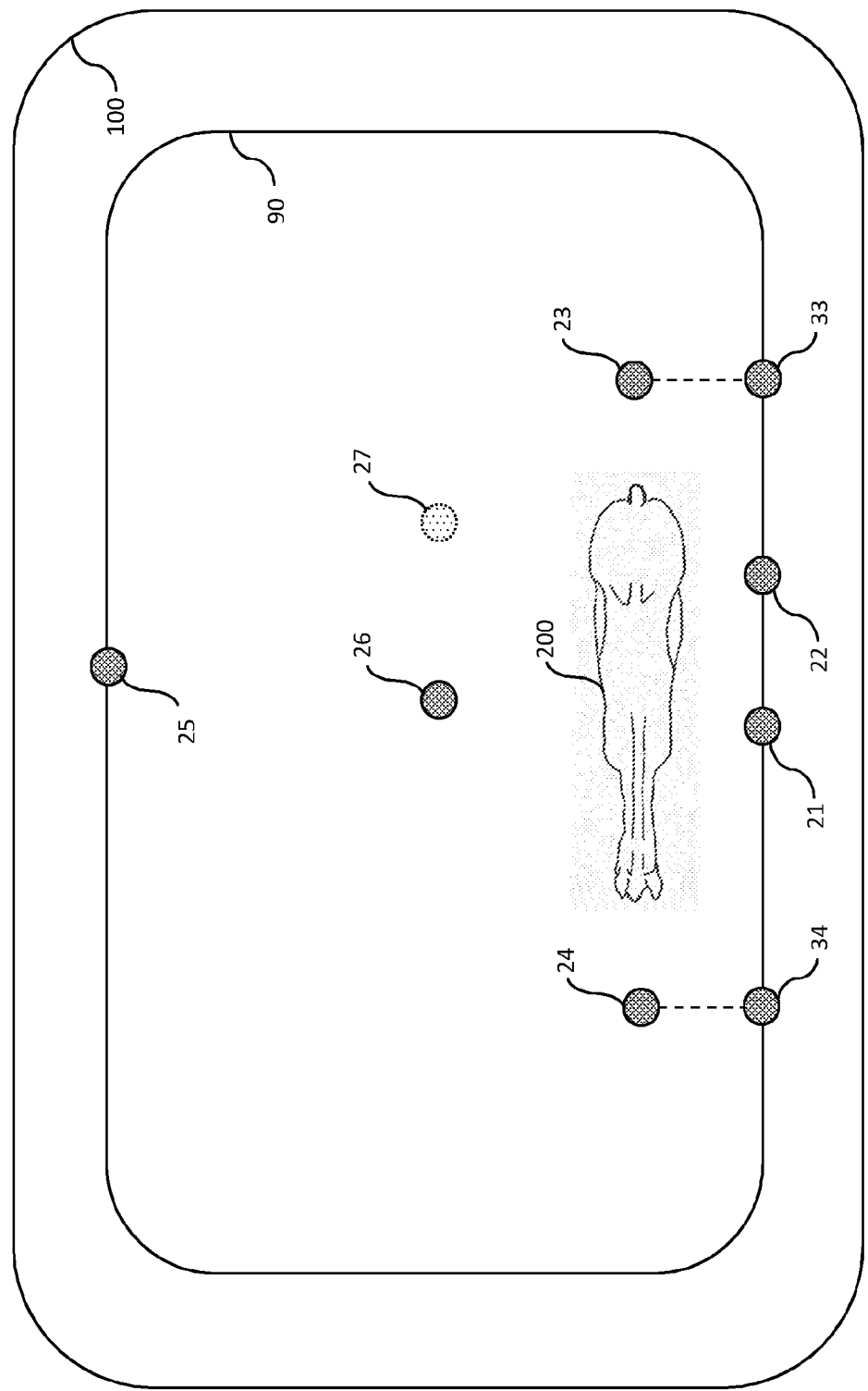
FIG. 3 shows a schematic illustration of the imaging system of FIG. 2 from a top view of the predefined area.

As shown in FIG. 3, optionally, a video camera 25 may be positioned so as to capture images from substantially the opposite side of the predefined area 100 to that of video cameras 21 and 22. Video camera 25 may provide a field of view from the entire side of the body of the horse 200 opposite to the side being filmed by video cameras 21 and 22. Video camera 25 may be stationary. Video camera 25 may be driven on the track 90 in a direction parallel to the direction of travel of video cameras 21 and 22. Video camera 25 may be driven on the track 90 in an opposite direction to the direction of travel of video cameras 21 and 22. Video camera 25 may be articulated to track the motion of the moving target at a location in between video cameras 21 and 22. Alternatively, video camera 25 may be configured to pinpoint video camera 26. When stationary, video camera 25 may be positioned off the track 90.

The images from one side of the horse 200 captured by video camera 25 when the horse 200 is moving in a first direction can be combined with the images of the same side of the horse 200 captured by video cameras 21 and 22 when the horse 200 is moving in a second direction opposite to the first direction to generate three-dimensional images of that side of the horse 200. Advantageously, such three-dimensional images would provide an examiner with a lot of useful information to aid in their study and assessment of the animal.

Optionally, anther video camera 27 may also be mounted at the top of the predefined area 100, spaced apart from video camera 26, so as to capture a second top view video footage of the moving target. Video camera 27 may be mounted on the ceiling. Video camera 27 may provide a field of view of the animal from around the head to around the back. Video camera 27 may thus provide information relating to the rider's movement and sitting position as well as to the saddle. Video camera 27 may be mounted to a rotatable supporting mechanism 37. Alternatively, the supporting mechanism 37 may be stationary.

Each video camera 21, 22, 23, 24, 25, 26, and 27 is mountable to a supporting mechanism 31, 32, 33, 34, 35, 36, and 37 respectively. The supporting mechanisms 31 to 37 may include an elongate portion 311, 321, 331, 341, 351, 361, and 371 extending from the supporting mechanisms 31 to 37 to support its mounted video cameras 21 to 27 substantially above, ahead, behind or to the side of the moving target. In addition, the elongate portions 311 to 371 help space apart the supporting mechanisms 31 to 37 and their respective mounted video cameras 21 to 27 from the track 90. In this way the video cameras 21 to 27 can be positioned to capture images from directly above, directly ahead, directly behind or directly to the side of the moving target to enable a full analysis of the subject's characteristics from various angles. This is particularly useful for assessing asymmetries in gait and conformation of horses that require direct comparison of the range of movement of two or more limbs and/or muscle groups.

The height of the elongate portions 311 to 371 may be adjusted to allow the video cameras 21 to 26 to be positioned at a suitable height in dependence on the type and size of the animal being tracked or in dependence on the feature of interest being captured (e.g. whether it is the limbs of the animal that are being assessed or its facial features). It is desirable to position the video cameras 21 to 27 at a suitable distance from the subject depending on a number of factors including, but not limited to: the video camera type, the animal type, the animal height, and/or the type of movement or manoeuvre being carried out, the particular aspect of animal being assessed, the field of view of interest, the track length or type.

The elongate portions 311 to 371 may include a pivot or a biasing means (not shown) that allows the elongate portion to fold away from the moving target, for example when not in use, or if hit by the moving target during use to prevent injury to the animal or person being tracked. The pivot may be a ball and socket joint, a hinge such as a sprung hinge or a resiliently deformable portion.

Each of the video cameras 21 to 27 may be provided with an articulating mechanism 51 to 57 (not shown) respectively. This provides the video cameras 21 to 27 with one or more degrees of freedom that allows the video cameras 21 to 27 to be independently articulated to aim at the moving target.

Each of the video cameras 21 to 24 are configured to move along with the moving target and thus are mountable onto support mechanisms 31 to 34 respectively which in turn comprise driving components 41 to 44 respectively (not shown). The cameras may be (i) configured so as to be capable of being driven to move in a generally horizontal direction with the intended track of the horse and/or (ii) configured so as to be driven to move together with the motion of the horse (e.g. at the same speed) so as to maintain their view on the respective parts of the horse and from respective directions. In this way video cameras 21 to 24 can be moved along the track system 90 around the perimeter of the predefined area 100. Supporting mechanism 31 to 34 and thus their corresponding video cameras 21 to 24 are independently movable. Advantageously this allows for dynamic adjustment to the distances between video cameras 21 to 24 and/or between the video cameras 21 to 24 and the horse 200 while the video cameras 21 to 24 are following the horse during a session. This is to account for any deviations of the animal from the track 90 and/or the ability of a rider to decide on the kinds of manoeuvres they'd like the horse 200 to perform on the spot.

Driving components 40 may have wheels which are slidably movable on the track system 90. The video cameras 20 may be mountable onto the supporting mechanisms 30 using a mount (not shown). In this way the video cameras 20 can be moved along the rail when mounted and be removed from the system when not in use. Different mounts may be provided with the system to accept different types of video camera 20. Universal mounts may be provided that can be adjusted to receive any video camera 20. Each video camera 20 is mounted securely to the supporting mechanism 30 and may include anti-vibration means for minimising vibration of the camera during movement along the track 90.

The track system 90 may be a rail such as a monorail. The rail may include a channel that is adapted to receive the supporting mechanisms 30. The rail may include or be adapted to receive a wheel or a roller that rolls along the rail to enable smooth, vibration reducing movement of the video cameras 20 along the track 90. The wheel or roller may be formed of or coated in a resiliently deformable material for reducing vibration. This has the advantage of creating sharper images and reducing sound while the video cameras 20 are being driven along the track 90, thus being less likely to startle the animal.

The driving components 40 may be electric motors. There may be a respective motor for driving each camera to move. Alternatively, a single motor may be provided to operate a pulley system that moves each supporting mechanism 30 along the rail. Alternatively, the rail may use an electric circuit to drive the supporting mechanisms 30. The rail and the supporting mechanisms 30 may include conductors that conduct electricity from a power source such as a battery or mains supply to drive the supporting mechanisms 30 that move the video cameras 20 along the track 90.

The video cameras 20 once mounted may be manually positioned (i.e. by manipulating the height and location of the mounts) on the track 90 by an operator. They may alternatively be positioned by the system controller 72 in dependence on a set of parameters input into the system via the user interface 82. These parameters may be input directly by the operator or determined by the system in dependence on such characteristics as the breed, age, size, and height of the animal provided to the system.

Typically, the video cameras 20 are arranged at a suitable distance from the moving target for a number of reasons including, but not limited to, potential deviation of the subject along the track 90 (to ensure images can be obtained even if the subject deviates from the centre of the track within a predetermined tolerance) and the manoeuvres being carried out. Suitably, the video cameras 20, their respective supporting mechanisms 30 and the track 90 may be covered with resilient rubber material so as to protect the animal from serious injury should the animal collide with them.

The imaging system includes a plurality of sensors 60 used to determine the motion of the moving target and/or the distance between the target and the video cameras 20 or the distance between the video cameras 20 and other objects. Once the initial video camera arrangement has been determined and the imaging system has been set up, the output of the sensors 60 are used by the controller 72 to command the video cameras 20 to track and/or follow the horse 200 while maintaining the initial video camera arrangement. The speed at which the video cameras 21 to 24 track and/or follow the horse 200 may be manually adjusted by an operator. Alternatively, the speed at which the video cameras 21 to 24 track and/or follow the horse 200 may be automatically determined by the controller 72 in dependence on the sensed motion of the horse 200 and/or the sensed distance between each of the video cameras 21 to 24 and the horse 200. This ensures that the video cameras 21 to 24 are moved at a speed that corresponds to the pace of the horse 200.

For example, a motion sensor may be provided on each of the video cameras 20 and the controller 72 may calculate a desired distance between the video cameras 20 based on the location data obtained from the motion sensors. This information can then be used by controller 72 to position and move the video cameras 20 along the track 90 whilst maintaining the desired distance between the video cameras 20 by sending commands to the driving components 40.

The driving components 40 of the supporting mechanisms 30 may be driven around the track 90 at any desired speed. The driving components 40 may be set to various working paces such as walking, trotting, cantering, galloping, etc.

The controller 72 controls and coordinates the functions of the various components of the imaging system 10 and processes the various data within the motion monitoring system. For example, the controller 72 is configured to control the video cameras 20 to track the moving target and it controls the driving components 40 to command the supporting mechanism 30 to follow the moving target. The controller 72 may be hardwired to the imaging system 10. Alternatively, the controller 72 may communicate with the imaging system 10 wirelessly. For example, the controller 72 may communicate wirelessly with each of the video cameras 21 to 24 to control the speed at which they move along the track 90 and/or the distance from the moving target or other video cameras that should be maintained.

Video cameras 20 may include a memory to store the captured images before this data is transferred to data storage 81. Alternatively, images captured by video cameras 20 may be wirelessly transmitted to memory 73 and/or data storage 81.

The imaging system 10 may include a thermal image capture device such as a thermal imaging camera (not shown) to monitor and record the temperature changes across the body of the moving target. Advantageously this information may help identify areas of inflammation or regions subjected to increase wear during movement. The temperature data can be obtained over a period of time to provide information on development of 'hot spots', the time taken to reach predetermined ranges and recovery times to starting temperatures.

Whilst the imaging system 10 has been described as having video cameras 20, it will be appreciated by those skilled in the art that any type of image capture device such as a dedicated camera or another device (e.g. a mobile handset, a tablet, etc.) incorporating a subsystem capable of capturing a video stream may be used in the present invention.

As well as equine motion monitoring, the motion monitoring and imaging systems described above are also applicable to the monitoring of other types of animals as well as human motion monitoring. The imaging system described above is suitable for indoor as well as outdoor use.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. An imaging system configured to generate video streams of a moving target in a predefined area, the imaging system comprising:
   first and second image capture devices configured to be movable and to capture first and second video streams of the moving target from a first direction;

third and fourth image capture devices configured to be movable and to capture third and fourth video streams of the moving target from a second and third directions, the second and third directions being substantially opposite to one another and substantially perpendicular to the first direction;

a fifth image capture device configured to be stationary and to capture a fifth video stream of the moving target from a fourth direction, the fourth direction being substantially perpendicular to the first to third directions; and a controller configured to move the first to fourth image capture devices concurrently along with the moving target in the predefined area.

2. The imaging system of claim 1, wherein each image capture device is configured to be movable independently of the other image capture devices.

3. The imaging system of claim 1, wherein each image capture device has a degree of freedom and the controller is configured to articulate each image capture device using that degree of freedom to track the motion of the moving target.

4. The imaging system of claim 1, wherein each image capture device is configured to be articulated independently of the other image capture devices.

5. The imaging system of claim 1, further comprising a sixth image capture device configured to capture a video stream of the moving target from a fifth direction, the fifth direction being substantially opposite to the first direction.

6. The imaging system of claim 5, wherein the controller is further configured to produce a three-dimensional (3D) video stream of the moving target using the video streams from the first, the second and the sixth image capture devices.

7. The imaging system of claim 1, wherein the sixth image capture device is stationary.

8. The imaging system of claim 1, further comprising a seventh image capture device spaced apart from the fifth image capture device and configured to capture a video stream of the moving target from the fourth direction.

9. The imaging system of claim 1, wherein the first and second image capture devices are positioned alongside each other.

10. The imaging system of claim 1, wherein the image capture devices are configured to be spaced apart from one another in dependence on the size of the moving target.

11. The imaging system of claim 1, wherein the controller is configured to maintain a relative distance between the image capture devices in dependence on the size of the moving target.

12. The imaging system of claim 1, wherein the first to fourth image capture devices are configured to be aligned horizontally.

13. The imaging system of claim 1, wherein each of the image capture devices is mountable onto a respective driving element.

14. The imaging system of claim 13, wherein each of the image capture devices are mountable onto their respective driving elements using a respective support mechanism.

15. The imaging system of claim 1, wherein each image capture device comprises a sensor, the sensor being configured to sense a distance between its image capture device and another object.

16. The imaging system of claim 15, wherein the controller is configured to determine a predefined distance between each image capture device and the other object in dependence on the sensed distance between each image capture device and the other object.

17. The imaging system of claim 15, wherein the controller is further configured to maintain a relative distance between each of the image capture devices and the other object in dependence on the determined predefined distance when the image capture devices are being moved.

18. The imaging system of claim 15, wherein the other object is another image capture device.

19. The imaging system of claim 15, wherein the other object is the moving target.

20. The imaging system of claim 1, further comprising a track covering the predefined area's perimeter along which the image capture devices are moved.

21. The imaging system of claim 20, wherein the first to fourth image capture devices are slidably mounted onto the track.

22. The imaging system of claim 1, wherein the controller is further configured to move the first to fourth image capture devices at a speed corresponding to the moving target's speed.

23. A motion monitoring system configured to assess the motion of an equine in motion, the motion monitoring system comprising the imaging system of claim 1, with the equine being the said moving target.

24. The motion monitoring system of claim 23, wherein the first to fourth image capture devices are configured to be aligned with the equine's limbs.

25. The motion monitoring system of claim 23, wherein the first image capture device is configured to provide a field of view of a lower aspect of a shoulder to a hoof surface of a foreleg of the equine.

26. The motion monitoring system of claim 23, wherein the first image capture device is configured to provide a field of view of an upper aspect of the ears to the shoulders of the equine.

27. The motion monitoring system of claim 23, wherein the second image capture device is configured to provide a field of view of a stifle to a hoof surface of a hindleg of the equine.

28. The motion monitoring system of claim 23, wherein the third image capture device is configured to provide a field of view of a lower aspect of the shoulders to the hooves of the forelegs and the chest of the equine.

29. The motion monitoring system of claim 23, wherein the fourth image capture device is configured to provide a field of view of the rump to the hooves of the hindlegs of the equine.

30. The motion monitoring system of claim 23, wherein the fifth and seventh image capture devices are configured to provide a field of view of the head to the rump of the equine.

31. The motion monitoring system of claim 23, wherein the sixth image capture device is configured to provide a field of view of one side of the equine opposite to that provided by the first and the second image capture devices.

32. A method of generating video streams of an equine in motion in a viewing zone of a predefined area, the method comprising:

capturing first and second video streams of the equine in motion from a first direction with a first and second image capture devices;

capturing third and fourth video stream of the equine in motion from a second and third directions with a third and fourth image capture devices, the second and third directions being substantially opposite to one another and substantially perpendicular to the first direction;

capturing a fifth video stream of the equine in motion from a fourth direction with a fifth image capture device, the fourth direction being substantially perpendicular to the first to third directions; and moving the first to fourth image capture devices concurrently along with the equine in motion in the predefined area.

\* \* \* \* \*